Figure 2:
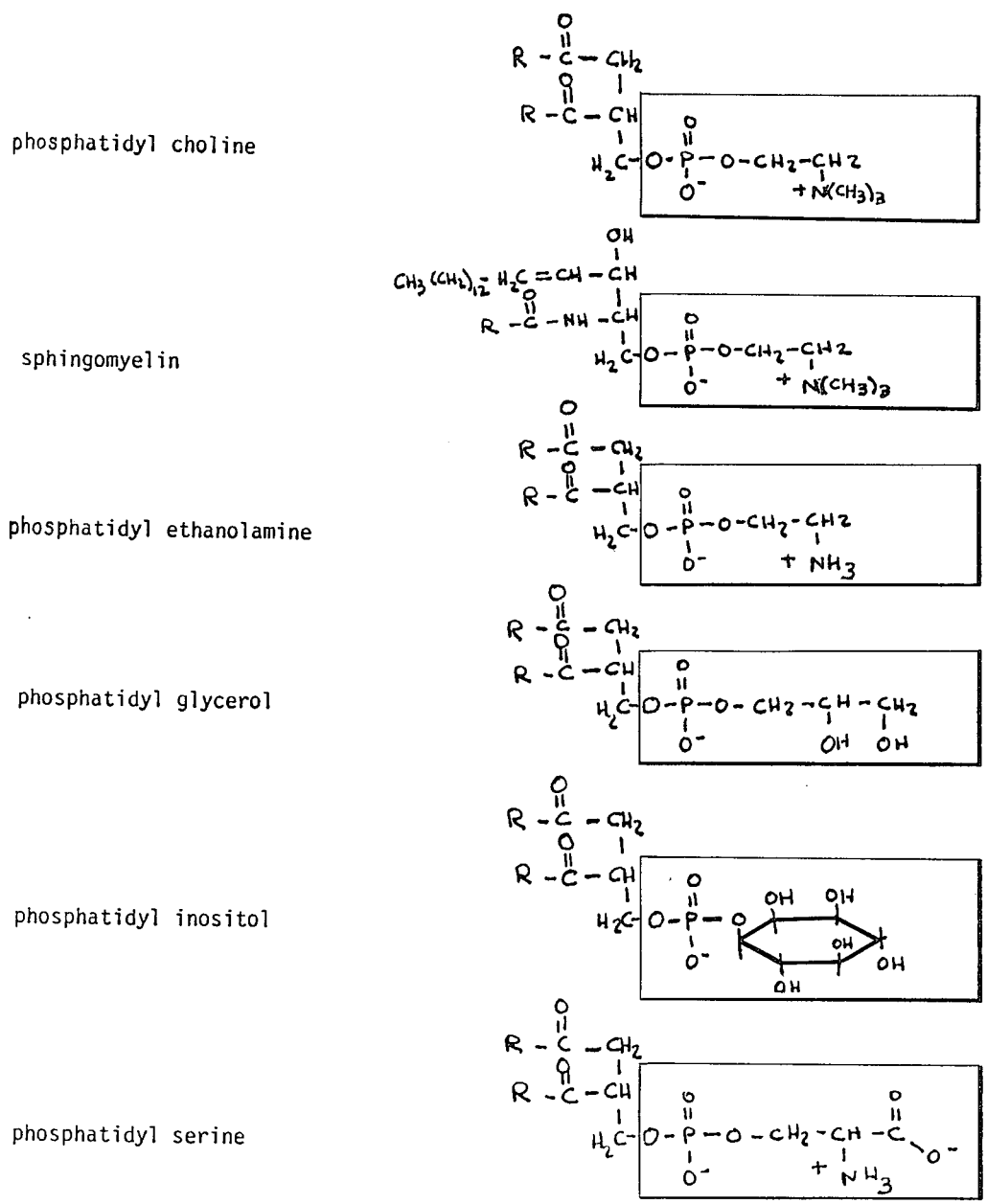

United States Patent [19]
Ilekis

[11] 4,370,311
[45] Jan. 25, 1983

[54] LIPID ASSAY BASED ON AGGREGATING PROPERTIES

[76] Inventor: John V. Ilekis, 6950 S. Campbell, Chicago, Ill. 60629

[21] Appl. No.: 271,952

[22] Filed: Jun. 9, 1981

[51] Int. Cl.³ .................... G01N 33/92; G01N 33/58
[52] U.S. Cl. .................................. 424/1.1; 436/13; 436/57; 436/71
[58] Field of Search ............... 23/230 B, 909; 424/1

[56] References Cited
U.S. PATENT DOCUMENTS

| | | | |
|---|---|---|---|
| 4,195,126 | 3/1980 | Hall | 435/11 |
| 4,211,531 | 7/1980 | Das | 23/909 X |
| 4,233,032 | 11/1980 | Statland | 23/230 B |

OTHER PUBLICATIONS

Chemical Abstracts, 82: 1311g, (1975).

*Primary Examiner*—Sidney Marantz
*Attorney, Agent, or Firm*—Kinzer, Plyer, Dorn & McEachran

[57] ABSTRACT

A simple and rapid method by which lipids can be measured quantitatively or qualitatively. The method involves the use of a labelled lipid of which one is interested in measuring or a different lipid reacting similarly to the lipid of interest. The labelled lipid is added to an unknown specimen and to a set of standard(s) containing various amounts of the lipid of interest. The label is allowed to interact. A portion of the label is then selectively removed of which the degree of the removal of the label is dependent upon the amount of the lipid initially present. The amount of lipid originally present in the unknown specimen can therefore be ascertained by extrapolating the amount of label present in the unknown specimen to the amount present in the identically treated standard(s).

6 Claims, 3 Drawing Figures

I. FORMATION OF AGGREGATING STRUCTURES

INCREASING AMOUNTS OF LIPID STANDARD    UNKNOWN
  A    B    C      X

II. ADDITION OF THE LABEL AND INCORPORATION INTO THE AGGREGATING STRUCTURE ( LABEL = ⊖— )

A    B    C    X

III. SEPARATION OF THE INCORPORATED LABEL FROM THE UNINCORPORATED LABEL

A    B    C    X

IV. EXTRAPOLATION OF THE AMOUNT OF LIPID IN THE SAMPLE BY THAT OF THE STANDARDS

V. RESULT

THE UNKNOWN TUBE CONTAINS B AMOUNT OF LIPID

FIG. I

I. FORMATION OF AGGREGATING STRUCTURES

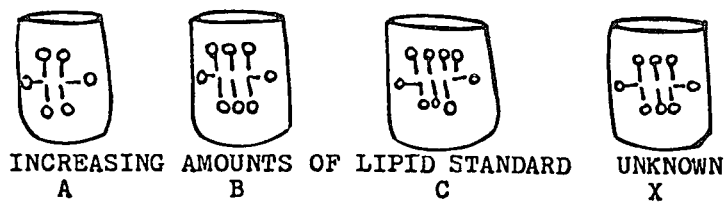

INCREASING AMOUNTS OF LIPID STANDARD    UNKNOWN
    A          B          C               X

II. ADDITION OF THE LABEL AND INCORPORATION INTO THE
    AGGREGATING STRUCTURE    ( LABEL = ●— )

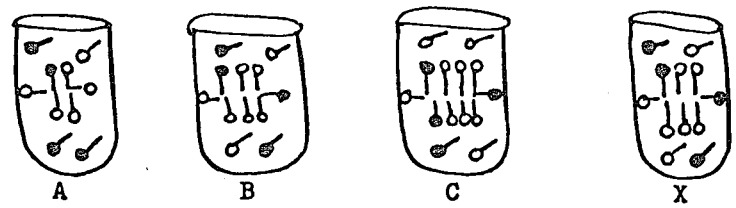

A          B          C               X

III. SEPARATION OF THE INCORPORATED LABEL FROM THE UN-
    INCORPORATED LABEL

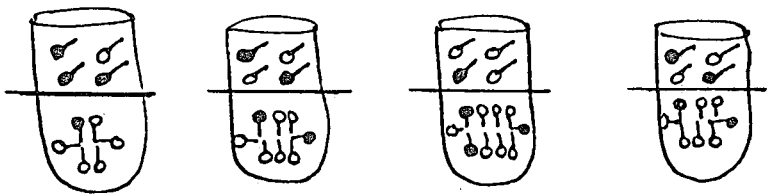

A          B          C               X

IV. EXTRAPOLATION OF THE AMOUNT OF LIPID IN THE SAMPLE
    BY THAT OF THE STANDARDS

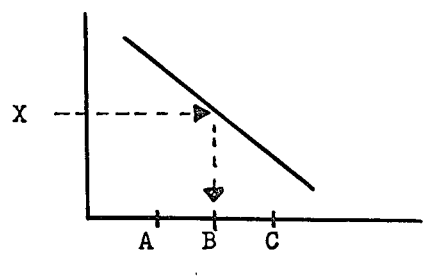

V. RESULT

THE UNKNOWN TUBE CONTAINS B AMOUNT OF LIPID

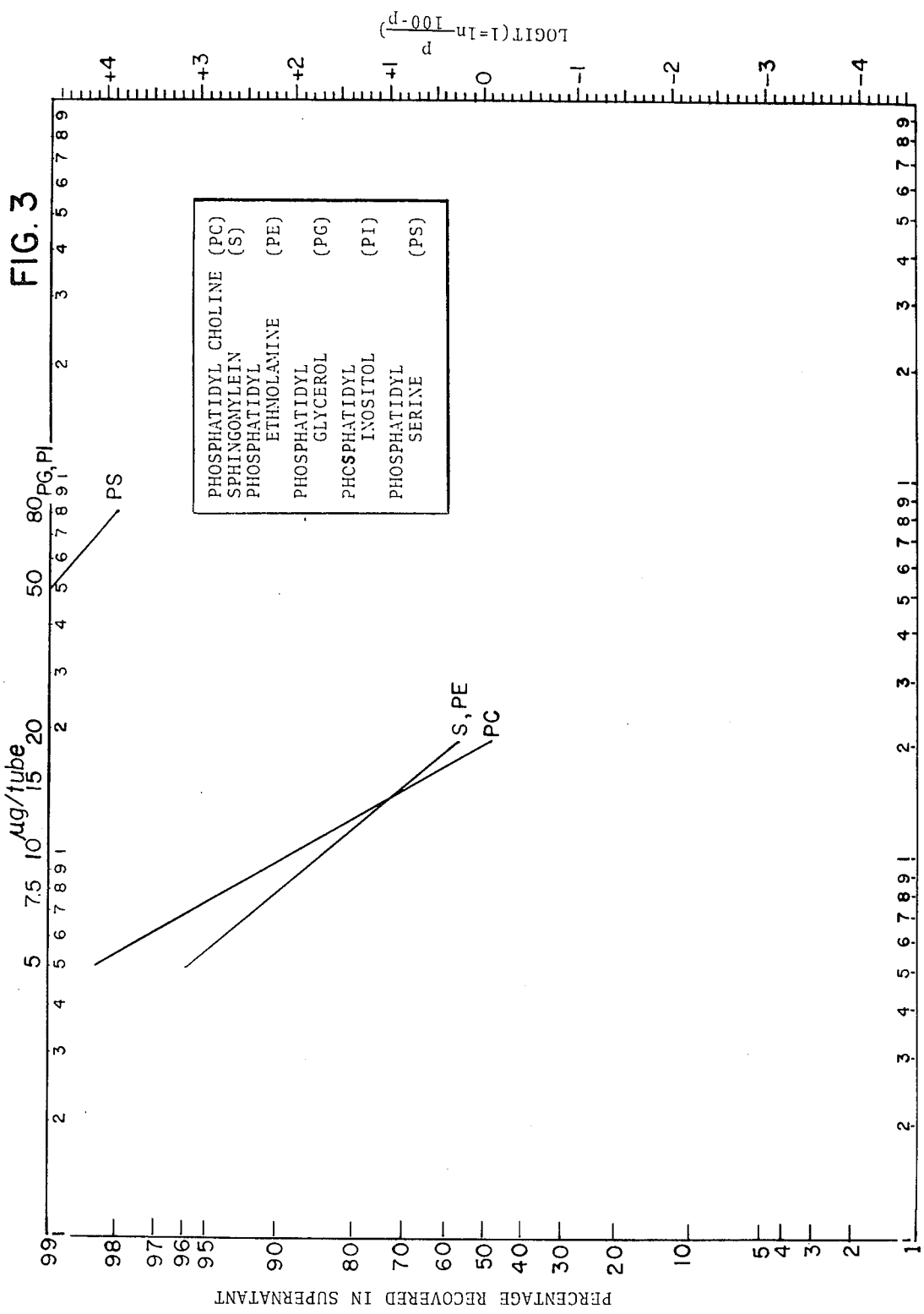

LIPID ASSAY BASED ON AGGREGATING PROPERTIES

The invention is concerned with the measurements of lipids in a supporting fluid.

As is well known, it is advantageous to be able to measure lipid concentrations. Because of their high concentrations in cell membrane and importance in particular physiological processes, considerable attention has focused on lipids. In the field of obstetrics, for example, the assessment of fetal lung maturity in complicated pregnancies for early delivery of the fetus is based on the measurements of lipids such as phospholipids in amniotic fluid.

The chemical structure of lipids allows them to form aggregates in solution such as miscelles, bilayers, or crystals (Fed. Proc. 29: 1320, 1970). The formation of a particular type of aggregate(s) is dependent on the chemical structure, the physical state, and the concentration of the particular lipid.

The invention is characterized in part by the incorporation of a labelled lipid into the above mentioned aggregate(s), the degree of incorporation being dependent on the amount of the particular lipid(s) forming the aggregating structure(s). Separation of the unincorporated label from the label incorporated within the aggregate(s) results in a differential amount of label recovered which is dependent on the amount of lipid initially present. Therefore in an identically treated unknown sample and standard(s) one can determine the amount of a lipid(s) present in the sample by extrapolation from the standard(s). Also, one can determine in a qualitative sense whether the unknown contains more or less than the standard used for comparison.

There are a large number of ways of carrying out this invention, including the following preferred method.

A method of determining the amount of a specific lipid(s) in an unknown fluid sample which comprises the steps of:
(a) Adding to the unknown sample a labelled lipid;
(b) Allowing a portion of the label to become incorporated in the sample;
(c) Measuring the amount of the label removed or unremoved from step (b);
(d) Calculating the amount of lipid present in the sample by the amount of label measured in step (c) by extrapolating from or comparison to an identically treated standard(s).

Preferably step (a) includes adding to the unknown the labelled lipid of interest, the label preferably being marked radioactive. Also, step (a) preferably includes adding a known amount of the labelled lipid to both the unknown sample and to the standard(s).

Step (b) preferably consists of selectively precipitating a portion of the label.

In order that the invention may be more fully understood, the following example of the measurement of certain lipids in a biological fluid is given by way of illustration only, and in the drawing:

FIG. 1 is a diagram of the preferred assay;
FIG. 2 shows the chemical structures of certain phospholipids, the polar head being boxed in;
FIG. 3 is a graph.

EXAMPLE

DETERMINATION OF PHOSHATIDYL CHOLINE, SPHINGOMYELIN, AND PHOSSPHATIDYL ETHANOLAMINE IN AMNIOTIC FLUID

Method

Into tubes containing 0.1 ml and 0.2 ml of an amniotic fluid sample is added 0.1 ml and 0.0 ml, respectively, of phosphate buffered saline. To the above amniotic samples tubes and to a set of standard tubes containing 0,5,7.5,10, 15 and 20,ug of dipalmoyl phosphatidyl choline in 0.2 ml of phosphate buffered saline is added 0.1 ml of radiolabelled $^{14}C$ dipalmoyl phoshatidyl choline (dpm=40,000, S.A.=114 millicuries/m mol) in 0.3% Triton-X in phosphate buffered saline. All the tubes are mixed vigorously and then incubated at 37° C. for 5–15 minutes. The tubes are then placed in an ice bath and to each is added 0.1 ml of icecold bovine gamma globulin solution (50 mg/ml in 0.1% Triton-X in phosphate buffered saline) followed by 1 ml of icecold precipitating solution. The tubes are mixed and then centrifuged for 5 minutes at 4° C. at 1000 xg. The supernatant of each tube is decanted into a scintillation vial, scintillation fluid is added, and the radioactivity is measured in a scintillation counter.

The precipitating solution is prepared as follows: 62.5 ml of 4% phosphotungstic acid (4 gr dissolved in 16 ml of 1 N sodium hydroxide and brought up to 100 ml with distilled water) is added 12.5 ml of 2 M $MgCl_2$, 25 ml of phosphate buffered saline, and 0.1 ml of Triton-X.

The amount of phosphatidyl choline, sphingomyelin, and phosphatidyl ethanolamine contained in the sample is calculated as follows: Constructing a standard curve on logit graph paper by plotting the cpm (counts of radioactivity per min) of each standard containing dipalmoyl phosphatidyl choline divided by the cpm of the 0 standard on the vertical ordinate versus the corresponding amount contained in each standard on the horizontal ordinate. The sample cpm is similarily divided by the cpm of the zero standard times 100%. The amount contained in each of the respective amniotic fluid tubes is then extrapolated from the standard curve. Each sample tube is then corrected for the amount assayed and the final value is given as an average.

In order to substantiate the validity of the invention the following validation study of the above method is presented as an illustration only.

To demonstrate the accuracy of the method known amounts of dipalmoyl phosphatidyl choline were added to five amniotic fluids (low in phosolipids) and assayed.

| dipalmoyl phosphatidyl choline added (ug/ml) | Exdogenous dipalmoyl phosphatidyl choline recovered (means ± SD) |
|---|---|
| 50 | 46 ± 5 |
| 100 | 89 ± 13 |
| 200 | 187 ± 4 |

Precision was determined by assaying two amniotic fluids a total of five times. The results are expressed as ug/ml (means±SD).

| amniotic fluid specimen | intra-assay variation | inter-assay variation |
|---|---|---|
| #1 | 66 ± 3 | 71 ± 3 |
| #2 | 135 ± 11 | 137 ± 6 |

To test the linearity of the method three amniotic fluid samples were assayed with varying dilutions. The results given below are corrected for each dilution and are expressed as ug/ml.

| dilution | sample #1 | sample #2 | sample #3 |
|---|---|---|---|
| — | 160 | 130 | 160 |
| 4/5 | 162 | 150 | 150 |
| 3/5 | 157 | 143 | 120 |
| 2/5 | 185 | 140 | 165 |

The specificity of the method is dependent upon the degree of structural similarity between the label and the standard. For example, phospholipids, although structurally similar, may have dissimilar polar head groups (refer to FIG. 2). Labelled phosphatidyl choline incorporates within phosphatidyl choline, sphingomyelin, and phosphatidyl ethanolamine, but not into phosphatidyl inositol, phosphatidyl glycerol, or phoshatidylserine (refer to FIG. 3). Therefore, this method is selective in that it allows only certain types of structurally similar phospholipids to be measured even in the presence of other structurally similar phospholipids.

In summary, and referring to FIG. 1, both the unknown and the standard (at I) are assumed to contain the same lipid aggregates in the same volume of fluid, but the standard (A,B,C), varies as to the mass (concentration) of the lipid aggregates in each sample while the concentration in the unknown sample is indeed unknown.

In the next step, II, identical amounts of the known lipid in radioactive form (e.g., shown as four moieties, as it were) are added to each sample and are allowed to incorporate into the aggregate in proportion to the mass of the aggregate present in the sample, this absorption or incorporation occurring by the Law of Mass Action.

In step III the radioactive lipid not absorbed, after waiting for equilibrium, is separated as a measure of what was absorbed, that is, it is a matter of choice whether one measures the absorbed, labelled material in the aggregate directly, or indirectly by difference.

Based on step III, a curve is drawn (FIG. 3) showing the mass action absorption character of the labelled lipid and against this curve one can determine the concentration in the unknown.

In another mode of practice, the qualitative mode, one merely compares the unknown to labelled A,B, or C, as the case may be, to determine if the unknown contains a lesser or greater concentration of lipid than the standard case whether it be A,B or C.

I claim:

1. A method for measuring the concentration of a lipid in a supporting fluid as an unknown and comprising:

A. selecting for assay a known volume of the sample containing the lipid for measurement and allowing that selected sample to absorb for test a measured amount of the same lipid in labelled form;

B. preparing a known concentration of the lipid as a standard separate from said selected sample;

C. adding to the separate standard a predetermined amount of the lipid in labelled form and allowing the standard to absorb the labelled lipid;

D. effecting separation of the absorbed and unabsorbed labelled lipid in both the sample and the standard and measuring the amount of lipid so absorbed in each of the sample and standard; and E. comparing the results of step A to the results of step D to determine if the unknown sample contains more or less or substantially the same as the standard.

2. A method according to claim 1 in which step B and step D are characterized by the use of several separate standards, each having a known, different concentration of the lipid, in which the measurements under step B are graphed and in which the comparison under step E is by an extrapolation applied to said graph.

3. The method of claim 1 wherein the fluid being assayed is amniotic fluid.

4. The method of claim 1 wherein the lipid being assayed is phosphatidyl choline, sphingomyelin or phosphatidyl ethanolamine.

5. The method of claim 1 wherein the separation is carried out by precipitation with a solution of phosphotungstic acid.

6. The method of claim 1 wherein the label is a radioactive label.

* * * * *